United States Patent
Viergutz et al.

[11] Patent Number: 6,015,903
[45] Date of Patent: Jan. 18, 2000

[54] METHOD OF RESOLVING RACEMIC MIXTURES

[75] Inventors: Wolfgang Viergutz, Ludwigshafen; Juergen Knopff, Minden; Walter Brase, Petershagen, all of Germany

[73] Assignee: BASF Aktiengesellschaft, Ludwigshafen, Germany

[21] Appl. No.: 09/029,363

[22] PCT Filed: Sep. 13, 1996

[86] PCT No.: PCT/EP96/04030

§ 371 Date: Feb. 26, 1998

§ 102(e) Date: Feb. 26, 1998

[87] PCT Pub. No.: WO97/11927

PCT Pub. Date: Apr. 3, 1997

[30] Foreign Application Priority Data

Sep. 26, 1995 [DE] Germany .................. 195 35 762

[51] Int. Cl.[7] .................................. C07D 217/20
[52] U.S. Cl. .................... 546/147; 546/149; 562/401; 564/335
[58] Field of Search ................. 546/149, 147; 564/335; 562/401

[56] References Cited

U.S. PATENT DOCUMENTS

| | | | |
|---|---|---|---|
| 4,120,964 | 10/1978 | Hartenstein | 424/258 |
| 5,199,970 | 4/1993 | Tompa | 504/225 |
| 5,453,510 | 9/1995 | Hill | 546/140 |
| 5,543,414 | 8/1996 | Nestor | 514/262 |

FOREIGN PATENT DOCUMENTS

| | | | |
|---|---|---|---|
| 202522 | 11/1986 | European Pat. Off. | |
| 1153578 | 5/1969 | United Kingdom | |
| 92/00965 | 1/1992 | WIPO | |

*Primary Examiner*—Evelyn Mei Huang
*Attorney, Agent, or Firm*—Keil & Weinkauf

[57] ABSTRACT

A process for resolving racemates of compounds of the formula I

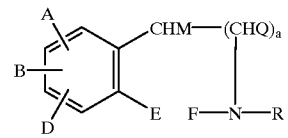

in which a, A, B, D, E, F, M, Q and R have the meanings given in the description is described. The process is carried in a manner known per se but using the optical antipodes of derivatives of phenoxypropionic acid.

Also described are salts of deprenyl, ephedrine or tetrahydropapaverine with a phenoxypropionic acid of the formula

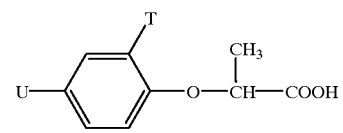

in which U and T have the meaning stated in the description, and which result as intermediate in the racemate resolution.

2 Claims, No Drawings

METHOD OF RESOLVING RACEMIC MIXTURES

This application is the national phase of PCT/EP96/04030, filed Sep. 13, 1996.

The present invention relates to a novel process for resolving racemates.

A large number of resolutions of racemates are already known. Despite this, resolutions of racemates repeatedly encounter problems because the resolving reagents are not sufficiently stable, result in oily antipodes which are difficult to isolate, can be used only in a very complicated manner, or show virtually no reaction with the racemates. There is thus a great interest in finding resolving reagents suitable for particular groups of racemates.

Tetrahydropapaverine is resolved into its antipodes for example with the aid of N-acetylleucine. This racemate resolution is a 3-stage process:

a) Precipitation of the S enantiomer with N-acetylleucine, b) Precipitation of the crude (required) R enantiomer with N-acetylleucine and c) Recrystallization of the R enantiomer bound to N-acetylleucine.

The crucial disadvantage of this process is that with N-acetylleucine virtually only the naturally occurring optically active acid is available for the resolution and this precipitates initially the unwanted diastereomeric S salt of tetrahydropapaverine. The salt of the R antipode can be precipitated only from the mother liquor enriched with this antipode.

It is also known that racemic 2-amino-1-butanol can be separated into its antipodes using (+)-2,4-dichlorophenoxypropionic acid.

We have now found a simpler process for resolving racemates.

The invention relates to a process for resolving racemates of compounds of the formula I

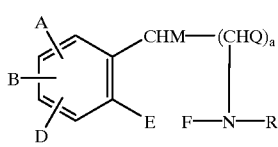

I in which the substituents have the following meanings:

a: 0 or 1

A: H, $C_{1-4}$-alkyl, $C_{1-4}$-alkoxy, halogen, nitro or amino,

B: H, $C_{1-4}$-alkyl, $C_{1-4}$-alkoxy, halogen, nitro or amino,

D: H, $C_{1-4}$-alkyl, $C_{1-4}$-alkoxy or halogen,

E: H,

F: H, $C_{1-4}$-alkyl, $C_{2-4}$-alkenyl, $C_{1-4}$-alkynyl or E and F together a radical of the formula III

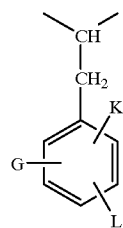

III in which

G: is H, $C_{1-4}$-alkyl, $C_{1-4}$-alkoxy, halogen, nitro or amino,

K: is H, $C_{1-4}$-alkyl, $C_{1-4}$-alkoxy, halogen, nitro or amino,

L: is H, $C_{1-4}$-alkyl, $C_{1-4}$-alkoxy or halogen,

M: H, $C_{1-4}$-alkyl or hydroxyl,

Q: H or $C_{1-4}$-alkyl,

R: H, $C_{1-4}$-alkyl or cyanomethyl, in a manner known per se, wherein the resolution is carried out with the optical antipodes of derivatives of phenoxypropionic acid of the formula II

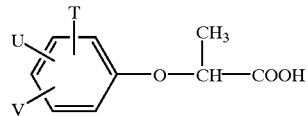

II in which T, U and V have the following meanings:

T: H, $C_{1-4}$-alkyl, $C_{1-4}$-alkoxy, halogen, nitro or cyano, or a phenyl ring which is unsubstituted, mono-, di- or trisubstituted by $C_{1-4}$-alkyl, $C_{1-4}$-alkoxy or halogen, U: H, $C_{1-4}$-alkyl, $C_{1-4}$-alkoxy, halogen, nitro or cyano, V: H, $C_{1-4}$-alkyl, $C_{1-4}$-alkoxy or halogen.

Suitable and preferred compounds of the formula I are those in which the substituents have the following meanings:

a: 1,

A: H or methoxy,

B: H or methoxy,

D: H,

E: H,

F: H, or

E and F together are a radical of the formula III in which G is H or methoxy, K is methoxy and L is H, M: H or methoxy, Q: methyl, R: H, methyl or cyanomethyl.

Particularly suitable compounds of the formula I are deprenyl, ephedrine and, in particular, tetrahydropapaverine. Suitable and preferred compounds of the formula II are those in which T is in the o position and is H, fluorine, chlorine or methoxy, U is fluorine, chlorine or methoxy in the p position, and V is hydrogen.

A particularly suitable compound of the formula II is (+)- or (−)-2-(2,4-dichlorophenoxy)propionic acid.

The racemate resolution can be carried out at from 0° C. to the boiling point of the solvent used. It is simplest to work at room temperature.

The resolution can be carried out in conventional solvents such as lower alcohols, acetone, toluene, xylenes, ethers, tetrahydrofuran and ethyl acetate. Saturated solutions are normally used. Isopropanol or toluene is preferably used.

The base can be liberated in aqueous solution at pH 7.5–10 from the salt produced in the racemate resolution, and can be extracted with a solvent which is insoluble in water, such as ether, toluene or a xylene.

The novel process is distinguished by the fact that the resolving reagents are easily obtainable and are stable. In addition, they have high selectivity and therefore provide the antipodes in good yields and in very high purity.

The invention also relates to the salts of deprenyl, ephedrine and tetrahydropapaverine with a phenoxypropionic acid of the formula

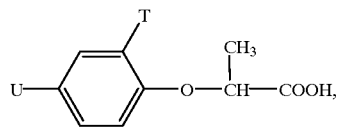

in which T is H, chlorine or methoxy and U is methoxy or chlorine. Among these, specific mention should be made of L-ephedrine D-dichlorophenoxypropionate and, in particular, (+)-THP D-2,4-dichlorophenoxypropionate.

EXAMPLE 1

1.029 g (3 mmol) of THP (THP=tetrahydropapaverine= 1-[(3,4-dimethoxyphenyl)methyl]-6,7-dimethoxy-1,2,3,4-tetrahydroisoquinoline) were taken up in 2 ml of isopropanol, a hot solution of 0.707 g (3 mmol) of D-2,4-dichlorophenoxypropionic acid in 8 ml of isopropanol was added, and the mixture was briefly refluxed. After cooling to room temperature, the resulting crystals were filtered off with suction, washed with isopropanol and dried. 0.9 g of a product which consisted predominantly of (+)-THP D-2,4-dichlorophenoxypropionate remained.

The resulting product was dissolved in 5 ml of water. The pH of the solution was adjusted to 8 and it was then extracted with toluene. After removal of the toluene, 0.48 g (93.3%) of the (+) enantiomer was obtained in an optical purity of 95.6%.

EXAMPLE 2

17.15 g (50 mmol) of THP were heated with 5.85 g (25 mmol) of D-2,4-dichlorophenoxypropionic acid in 80 ml of isopropanol with stirring. A clear solution was obtained at 45° C. At 50° C., the solution was seeded with the (+) isomer of the salt. The solution was then cooled to room temperature over the course of 2 h with stirring. 40 ml of isopropanol were also added for dilution. The crystals which separated out were filtered off with suction, washed with 30 ml of isopropanol and dried. The THP was liberated as in Example 1 from the salt obtained in this way.

5.2 g (61%) of (+)-THP were obtained with an optical purity of 90.1%.

EXAMPLE 3

1.715 g (5 mmol) of THP and 0.588 g (2.5 mmol) of D-2,4-dichlorophenoxypropionic acid were dissolved in 10 ml of toluene at the reflux temperature and then slowly cooled. The resulting crystals were filtered off with suction and dried. (+)-THP was isolated as in Example 1. 0.85 g (98.8%) of (+)-THP was obtained. The optical purity was 96.1%.

EXAMPLE 4

A solution of 17.15 g (50 mmol) of THP in 55 ml of toluene at 60° C. was stirred with a solution of 5.88 g (25 mmol) of D-2,4-dichlorophenoxypropionic acid in 55 ml of toluene at 60° C. and induced to crystallize. The crystals were filtered off with suction and thoroughly washed with toluene and then dried.

The crystals were worked up to (+)-THP as in Example 1. The yield was 8.6 g (98.3%), and the optical purity of the (+)-THP was 98.7%.

EXAMPLE 5

8.25 g (50 mmol) of D,L-ephedrine and 5.88 g (25 mmol) of D-2,4-dichlorophenoxypropionic acid were taken up in 100 ml of toluene. Heating to reflux was followed by slow cooling, and the crystals were filtered off with suction and washed with toluene. Drying resulted in 4.2 g (42%) of ephedrine salt. Liberation of the base as in Example 1 and conversion thereof into the hydrochloride resulted in L-ephedrine hydrochloride in an overall yield of 40%, $[\alpha]_D^{20}$: −33.7°.

We claim:

1. A process for resolving tetrahydropapaverine by reacting tetrahydropapaverine with (+)- or (−)-2-(2,4-dichlorophenoxy)propionic acid, separating a diastereoisomer from the obtained mixture of diastereoisomers, recovering an isomeric form of tetrahydropapaverine from the separated diastereoisomer.

2. (+)-THP D-2,4-dichlorophenoxypropionate.

* * * * *